United States Patent
Yokota et al.

(10) Patent No.: US 8,187,188 B2
(45) Date of Patent: May 29, 2012

(54) IMAGE PROCESSING APPARATUS, IMAGE PROCESSING PROGRAM, STORAGE MEDIUM AND ULTRA-SONOGRAPH

(75) Inventors: Yasunari Yokota, Gifu (JP); Fumio Nogata, Gifu (JP); Yoko Kawamura, Gifu (JP)

(73) Assignee: Gifu University (JP)

( * ) Notice: Subject to any disclaimer, the term of this patent is extended or adjusted under 35 U.S.C. 154(b) by 129 days.

(21) Appl. No.: 12/808,487

(22) PCT Filed: Mar. 24, 2008

(86) PCT No.: PCT/JP2008/055361
§ 371 (c)(1),
(2), (4) Date: Jun. 16, 2010

(87) PCT Pub. No.: WO2009/081599
PCT Pub. Date: Jul. 2, 2009

(65) Prior Publication Data
US 2011/0112402 A1 May 12, 2011

(30) Foreign Application Priority Data
Dec. 20, 2007 (JP) ................................ 2007-328325

(51) Int. Cl.
*A61B 8/00* (2006.01)
(52) U.S. Cl. ........ 600/441; 600/437; 600/443; 600/453; 382/131
(58) Field of Classification Search .......... 600/437–466; 382/128–132
See application file for complete search history.

(56) References Cited

U.S. PATENT DOCUMENTS

| 6,132,373 | A | 10/2000 | Ito et al. |
| 6,554,774 | B1 * | 4/2003 | Miele ............................ 600/485 |
| 7,048,691 | B2 * | 5/2006 | Miele et al. ................... 600/504 |
| 7,074,187 | B2 | 7/2006 | Selzer et al. |
| 7,503,896 | B2 * | 3/2009 | Miele et al. ................... 600/454 |
| 2002/0055680 | A1 * | 5/2002 | Miele et al. ................... 600/450 |
| 2002/0062086 | A1 * | 5/2002 | Miele et al. ................... 600/483 |
| 2005/0038346 | A1 * | 2/2005 | Miele ............................ 600/485 |

(Continued)

FOREIGN PATENT DOCUMENTS
JP 2002209857 A 7/2002
(Continued)

OTHER PUBLICATIONS
Office Action dated Apr. 27, 2011 re Australian Application No. 2008341769.
(Continued)

*Primary Examiner* — Sanjay Cattungal
(74) *Attorney, Agent, or Firm* — Caesar, Rivise, Bernstein, Cohen & Pokotilow, Ltd.

(57) ABSTRACT

A computer 12 of an image processing apparatus 11 acquires ultrasound B-mode images of consecutive frames to estimate a carotid artery wall at a carotid artery minor axis cross section included in an ultrasound B-mode image of a predetermined frame. The computer 12 also uses, as a template image, the ultrasound B-mode image, which includes the estimated carotid artery wall and surrounding tissues of the carotid artery wall and estimates the size of the diameter of the carotid artery wall so as to minimize a margin of error between a transformed template image, which is created by transforming the template image, and the acquired ultrasound B-mode image of each frame, thereby acquiring the time change of the carotid artery wall.

7 Claims, 8 Drawing Sheets

U.S. PATENT DOCUMENTS

2006/0206032 A1* 9/2006 Miele et al. .................. 600/504
2009/0012399 A1* 1/2009 Sunagawa et al. ............ 600/454

FOREIGN PATENT DOCUMENTS

| JP | 2005-185575 A | 7/2005 |
|---|---|---|
| JP | 2006166955 A | 6/2006 |
| JP | 3882084 B2 | 11/2006 |
| JP | 2007268303 A | 10/2007 |
| JP | 2009-66268 A | 4/2009 |

OTHER PUBLICATIONS

Nakagawa, N. et al., "Imaging of Cross-Sectional Elastacity in Short-Axis Plane of Arterial Wall by Transcutaneous Ultrasound," 2003 IEEE Ultrasonics Symposium Proceedings, Honolulu, Hawaii, Oct. 5, 2003-Oct. 8, 2003 New York, NY: IEEE, US, vol. 2, Oct. 5, 2003, pp. 1887-1890.
European Search Report re Application No. EP 08 72 2677 dated Mar. 18, 2011.
International Preliminary Report on Patentability for PCT/JP2008/055361 issued Jul. 20, 2010.
International Search Report for PCT/JP2008/055361.
Fumio Nogata, et al., "Study on a system . . . ", May 22, 2007, pp. 121-124.
Fumio Nogata, et al., "A new system . . . ", Mar. 16, 2007, pp. 195-196.
Takayuki Kato, et al., "Mechanical reliability . . . ", Feb. 10, 2006, pp. 177-180.
Hiroyuki Sugimoto, et al., "Mechanical Properties . . . ", Mar. 1, 2002, No. 033-1, pp. 233-234.
Harada, A., "Measurement of Arteriosclerosis . . . ", vol. 28(3), pp. 29-35, 2003.
GH. Granlund, "Fourier Preprocessing . . . ", vol. C-21, pp. 195-201, 1972.
Chris L. de Korte, et al., "Characterization of Plaque . . . ".
Radj A. Baldewsing, Chris L. deKorte, et al., "Comparison of Finite . . . ", pp. 1921-1924, 2002.
Hayashi, K., "Anatomy of Japanese . . . ", Bunkyo Shoin, 1965, pp. 9.

* cited by examiner

$r_1$: INNER RADIUS (mm)
$r_2$: OUTER RADIUS (mm)
P: INTERNAL PRESSURE (kPa)
$E_1$, $E_2$: ELASTIC MODULUS (kPa)
$v_1 = v_2 = 0.5$: POISSON'S RATIO

IMAGE PROCESSING APPARATUS, IMAGE PROCESSING PROGRAM, STORAGE MEDIUM AND ULTRA-SONOGRAPH

FIELD OF THE INVENTION

The present invention relates to an image processing apparatus, an image processing program, a storage medium, and ultrasonic diagnostic equipment, and particularly, to an image processing apparatus and an image processing program for an ultrasound image of a carotid artery as well as a storage medium and ultrasonic diagnostic equipment related to the image processing apparatus and the image processing program.

BACKGROUND OF THE INVENTION

Arteriosclerosis is one of the lifestyle-related diseases in which excessive lifestyle habits are risk factors. Arteriosclerosis advances from youth with very few symptoms, and if left untreated, arteriosclerosis may develop into cerebral infarction, cardiac infarction, angina pectoris, and the like. It is difficult to cure arteriosclerosis. Therefore, it is important to find symptoms of arteriosclerosis at an early stage and prompt the patients to improve lifestyle habits to slow down the progression of the diseases.

There are various diagnostic methods for examining arteriosclerosis. Among the methods, ultrasonic echo examination allows noninvasive direct observation of blood vessels and has been gaining a foothold as an indispensable examination in the current clinical diagnosis. The ultrasonic echo examination for arteriosclerosis diagnosis evaluates the presence of fat called plaque adhered inside blood vessels and intima-media complex thickness (IMT). However, at an early stage of arteriosclerosis, there is no plaque, and the IMT is thin and hard to measure. It is difficult to find symptoms at an early stage in such a morphological observation.

As contrasted with this, since arteriosclerosis is sclerosis of artery and a loss of elasticity, there is an idea that movements of artery associated with heartbeats can be evaluated. Unlike the morphological measurements such as plaque and IMT measurements, the aid of computer is inevitable when performing a quantitative measurement of the movements of artery.

Patent Document 1 discloses that measurement of variation in the carotid artery diameter associated with heartbeats can obtain an indicator of arteriosclerosis.

In Japanese Patent Application No. 2007-239198, the present applicant proposes a method of using an ultrasound B-mode major axis cross-sectional image to estimate variation in the carotid artery diameter associated with heartbeats. The method is executed based on a precondition that the carotid arteries are homogenous regardless of the positions on the major axis (y axis) and show equivalent variations according to heartbeats. Although satisfied in many cases, the precondition is not satisfied in a case where there is local arteriosclerosis in the carotid artery. Therefore, in such a case, the method previously proposed by the present applicant cannot be applied. The major axis of a carotid artery is an axis extending in an extension direction of the carotid artery, and an axis orthogonal to the major axis is referred to as a minor axis of the carotid artery.

In a case where there is local arteriosclerosis in a carotid artery, a minor axis cross-sectional image of the carotid artery, which is an ultrasound B-mode image, can be used to estimate variation in a carotid artery associated with heartbeats. However, the size of one pixel of the ultrasound B-mode image is about 0.07 to 0.11 mm, and the resolution is sufficiently high. Therefore, a technique for capturing the variation in a carotid artery with accuracy finer than the size of one pixel is indispensable.

In a method proposed by the present application in Japanese Patent Application No. 2007-239198, information related to a spatial shape of a carotid artery major axis cross-sectional image is used to improve the estimation accuracy. However, when a minor axis cross-sectional image of a carotid artery is used, it is difficult to use information related to a spatial shape of the image to improve the estimation accuracy due to the following reasons. The first reason is that although the minor axis cross section shapes of a carotid artery are substantially circular, individual differences are large. Therefore, it is difficult to express the shapes uniformly. The second reason is that the area occupied by the carotid artery in an ultrasound B-mode image is smaller in a minor axis cross-sectional image than in a major axis cross-sectional image. Therefore, usable information is scarce.

Non-Patent Document 1 proposes a method of manually designating a point on a carotid artery wall on a B-mode image, and then using an RF signal to estimate and track the movement of the designated point on the carotid artery wall in 10 µm accuracy. The method is in practical use.

When an RF signal is used as in the method proposed in Non-Patent Document 1, the estimation accuracy can be improved using a phase difference tracking method with an increased sampling rate. However, such a method for improving the estimation accuracy cannot be applied to a method of using a B-mode image to estimate and track the movement of a carotid artery. Furthermore, when the movement of a carotid artery is tracked, it is advantageous to use an RF signal from the viewpoint of accuracy. However, ultrasonic diagnostic equipment capable of outputting RF signals is limited to only some models. The ultrasonic diagnostic equipment therefore cannot be regarded as being in common use and lacks versatility.

Patent Document 1: Japanese Patent No. 3882084
Non-Patent Document 1: Harada A, "Measurement of Arteriosclerosis Indicator by Echo-Tracking Method (in Japanese)", Japanese Journal of Medical Ultrasound Technique, Vol. 28(3): pp. 29-35, 2003.
Non-Patent Document 2: G. H. Granlund, "Fourier preprocessing for hand print character recognition", IEEE Trans. on Computers, Vol. C-21, pp. 195-201, 1972.
Non-Patent Document 3: Chris L. de Korte et al, "Characterization of Plaque Components with Intravascular Ultrasound Elastgraphy in Human Femoral and Coronary Arteries In Vitro".
Non-Patent Document 4: Radj A. Baldewsing, Chris L. de Korte et al. "Comparison of Finite Elements Model Elastograms and IVUS Elastograms acquired from Phantoms and Arteries", IEEE Symposium, pp. 1873-1875, 2002.
Non-Patent Document 5: Hayashi K, "Anatomy of Japanese and Japanese Medical Experimental Animals and Physiological Modulus (in Japanese)", Second Edition (corrected reprint edition), Bunkyo Shoin, pp. 9, 1965.

SUMMARY OF THE INVENTION

Accordingly, an objective of the present invention is to provide an image processing apparatus and an image processing program capable of using an ultrasound B-mode image to track variation in a carotid artery associated with heartbeats with sufficient accuracy even if there is local arteriosclerosis in the carotid artery. Another objective of the present invention is to provide a storage medium storing the image processing program and ultrasonic diagnostic equipment connected to the image processing apparatus for use.

To achieve the foregoing objectives, a first aspect of the present invention provides an image processing apparatus comprising: carotid artery wall estimation means that acquires ultrasound B-mode images of consecutive frames to estimate a carotid artery wall at a carotid artery minor axis cross section included in an ultrasound B-mode image of a predetermined frame; and heart rate variability tracking means that uses, as a template image, the ultrasound B-mode image including the estimated carotid artery wall and surrounding tissues of the carotid artery wall and estimates the size of the diameter of the carotid artery wall so as to minimize a margin of error between a transformed template, which is created by transforming the template image, and the acquired ultrasound B-mode image of each frame, thereby acquiring a time change of the carotid artery wall.

Preferably, the carotid artery wall estimation means determines the value of a carotid artery parameter for determining the position and the shape of the carotid artery so as to maximize an evaluation function indicating a degree of probability of a carotid artery, thereby estimating the carotid artery wall.

Preferably, the heart rate variability tracking means also estimates a deviation if there is a deviation in the center of the carotid artery on the ultrasound B-mode image in each frame.

A second aspect of the present invention provides an image processing program causing a computer to function as: carotid artery wall estimation means that acquires ultrasound B-mode images of consecutive frames to estimate a carotid artery wall at a carotid artery minor axis cross section included in an ultrasound B-mode image of a predetermined frame; and heart rate variability tracking means that uses, as a template image, the ultrasound B-mode image including the estimated carotid artery wall and surrounding tissues of the carotid artery wall and estimates the size of the diameter of the carotid artery wall so as to minimize a margin of error between a transformed template image, which is created by transforming the template image, and the acquired ultrasound B-mode image of each frame, thereby acquiring a time change of the carotid artery wall.

Preferably, the carotid artery wall estimation means determines the value of a carotid artery parameter for determining the position and the shape of the carotid artery so as to maximize an evaluation function indicating a degree of probability of a carotid artery, thereby estimating the carotid artery wall.

Preferably, the heart rate variability tracking means also estimates a deviation if there is a deviation in center of the carotid artery on the ultrasound B-mode image in each frame.

A third aspect of the present invention provides a storage medium storing the image processing program according to the second aspect.

A fourth aspect of the present invention provides ultrasonic diagnostic equipment connected to the image processing apparatus according to the first aspect. The ultrasonic diagnostic equipment generates an ultrasound B-mode image based on an echo signal obtained through transmission and reception of ultrasound by a probe and outputs the generated ultrasound B-mode image to the image processing apparatus.

DETAILED DESCRIPTION OF THE PREFERRED EMBODIMENTS

Hereinafter, one embodiment of the present invention will be described with reference to FIGS. 1 to 13(l).

Figure 1:
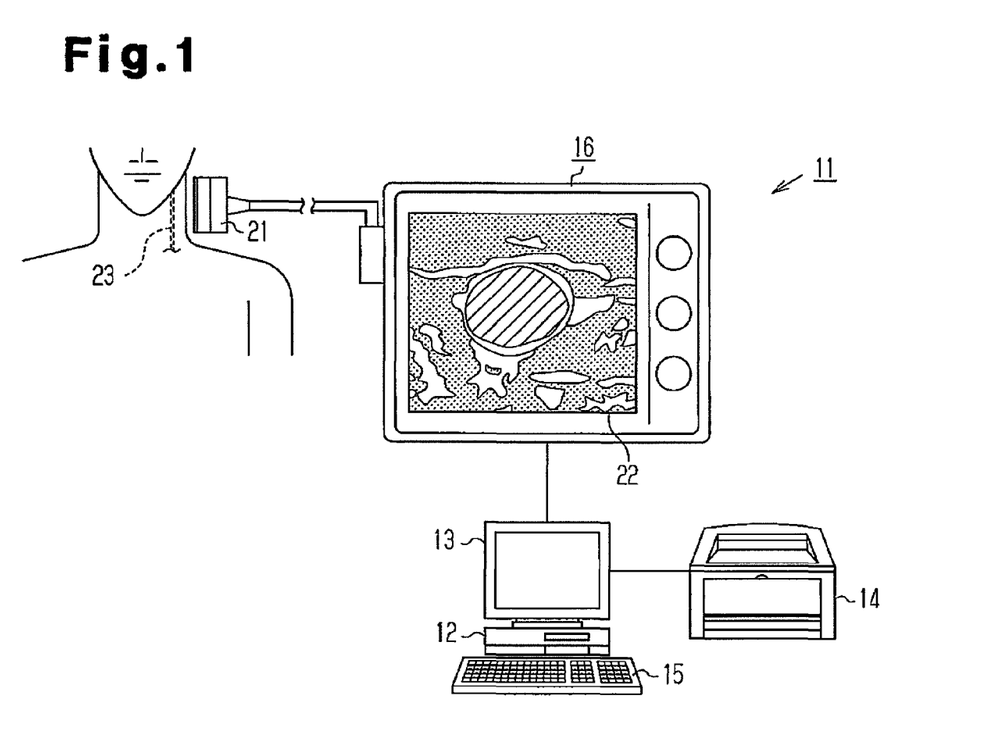
FIG. 1 is a schematic diagram of an image processing apparatus according to one embodiment of the present invention.

As shown in FIG. 1, an image processing apparatus 11 of the present embodiment comprises a computer 12, a display 13, a printer 14, a keyboard 15, and ultrasonic diagnostic equipment 16. The computer 12 functions as carotid artery wall estimation means (carotid artery wall estimation unit) and heart rate variability tracking means (heart rate variability tracking unit).

Figure 5:
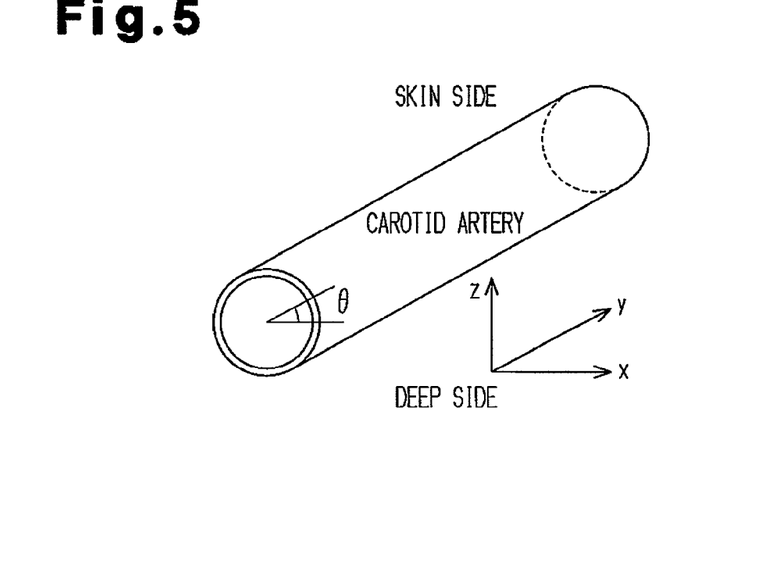
FIG. 5 is a diagram showing a coordinate system in a carotid artery minor axis cross section.

The ultrasonic diagnostic equipment 16 comprises a probe 21, a display part 22, and an ultrasound source (not shown). The probe 21 of the ultrasonic diagnostic equipment 16 includes a tip end surface for transmitting a pulse wave in a living body and for receiving reflected waves (echo signal) from a carotid artery 23. The tip end surface of the probe 21 is formed in a rectangular shape. The ultrasonic diagnostic equipment 16 generates echo moving images (thus, a plurality of ultrasound B-mode images) that are acquired in a B-mode based on the echo signal and include carotid artery minor axis cross sections. The display part 22 of the ultrasonic diagnostic equipment 16 displays variations, such as expansion and contraction, of the carotid artery 23 of a subject in moving images. FIG. 5 shows a coordinate system in the carotid artery minor axis cross section.

The ultrasound B-mode images are outputted from a video output of the ultrasonic diagnostic equipment 16, video captured by a DV converter (not shown) in a predetermined resolution (m×n pixels) and predetermined frames per second, and then inputted to the computer 12 as an IEEE 1394 signal. Although 30 frames/second is selected as the predetermined frames per second in the present embodiment, the value is not limited to this. The value can be any value as long as it allows clear observation of variation in the carotid artery associated with heartbeats.

The number of pixels of an ultrasound image region displayed on the display 13 is represented by Nx in the horizontal direction and Ny in the vertical direction. In the present embodiment, although Nx=540 (pixels) and Ny=420 (pixels) are selected, the numbers are not limited.

The echo moving images acquired by the ultrasonic diagnostic equipment 16 are inputted to the computer 12, and then stored in a storage device 44 (see FIG. 2) incorporated in the computer 12. The storage device 44, which is made up of, for example, a hard disk or a semiconductor storage device, can read and write various information.

Figure 2:
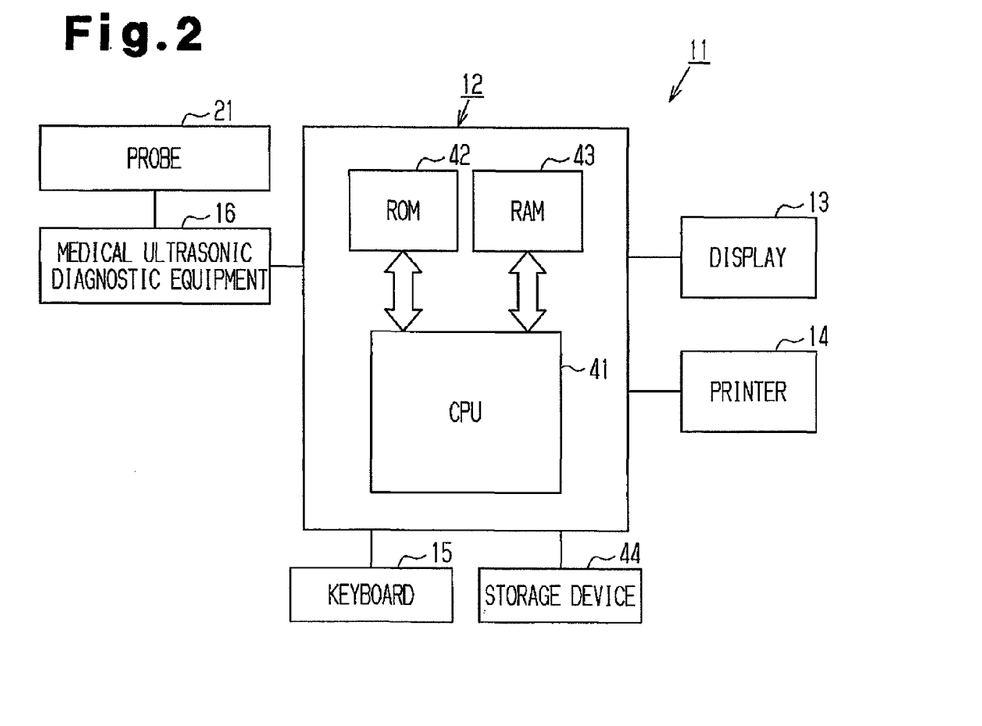
FIG. 2 is a schematic electrical block diagram of the image processing apparatus of FIG. 1.

As shown in FIG. 2, the computer 12 includes a central processing unit (CPU) 41, a ROM 42, and a RAM 43 and executes an image processing program stored in the ROM 42 as a storage medium. The RAM 43 is a working memory for executing the program.

Operation of Embodiment

Next, a process of the image processing program executed by the CPU 41 in the image processing apparatus 11 configured as described above will be described. Before the description of the program processing, "stress and distortion characteristics of carotid artery and surrounding tissues", "two-layer cylindrical model", and "summary of method for tracking heart rate variability of carotid artery wall" will be described.
(Stress and Distortion Characteristics of Carotid Artery and Surrounding Tissues)

Carotid arteries repeat expansion and contraction by heartbeats. Surrounding tissues, such as fat, around the carotid arteries expand and contract in association with the expansion and contraction of the carotid arteries. In general, the relationship between the stress and distortion of substance is examined from the perspective of strength of materials.

Figure 3:
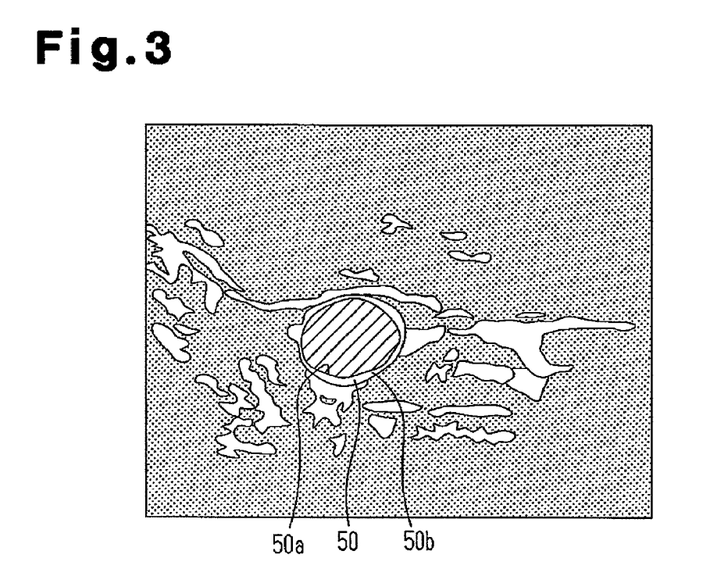
FIG. 3 is a diagram showing an ultrasound B-mode image including a carotid artery minor axis cross section.

FIG. 3 shows an ultrasound B-mode image (hereinafter, also simply referred to as "image") including a carotid artery minor axis cross section. A circular carotid artery 50 is shown at substantially the center in FIG. 3. In the ultrasound B-mode image, a carotid artery lumen 50a hatched in FIG. 3 is depicted in black, and a carotid artery wall 50b is depicted in white. The carotid artery is surrounded by surrounding tissues such as fat.
(Two-Layer Cylindrical Model)

Figure 4:
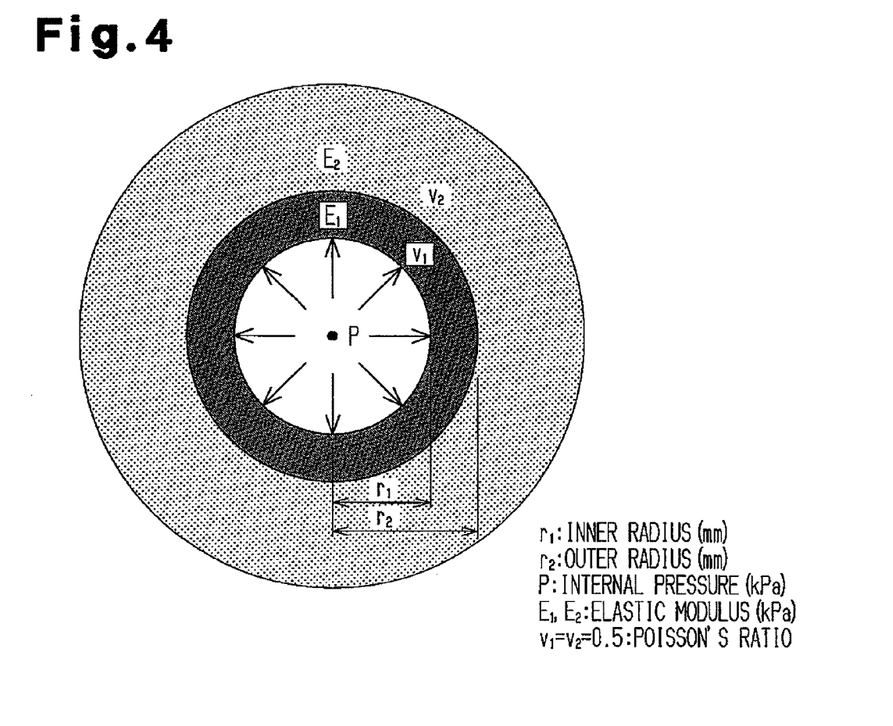
FIG. 4 is an explanatory diagram of a two-layer cylindrical model.

The carotid artery and the surrounding tissues can be modeled with a uniform two-layer cylinder (also referred to as "two-layer thick cylinder" in terms of strength of materials) as shown in FIG. 4. An inner radius of a carotid artery wall is designated by $r_1$, and an outer radius is designated by $r_2$. It is assumed that the surrounding tissues exist from the position apart from the center of the carotid artery by the length of $r_2$ to the infinity. Elastic modulus of the carotid artery wall is designated by $E_1$, and elastic modulus of the surrounding tissues is designated by $E_2$. A Poisson's ratio $v_1$ of the carotid artery wall and a Poisson's ratio $v_2$ of the surrounding tissues are both assumed to be 0.5. The amount of displacement d(r) with respect to a radial direction of the carotid artery and the surrounding tissues when there is a change in the internal pressure (blood pressure) of the carotid artery from a specific reference state, in which the inner radius of the carotid artery wall is expressed by $r_1$ and the outer radius is expressed by $r_2$, can be expressed by the following Theoretical Equation (1) of a two-layer cylindrical model. In Equation (1), reference character P denotes the amount of change in the internal pressure from the reference state.

$$d(r; P, r_1, r_2, E_1, E_2) = \begin{cases} \dfrac{3(r^2(-E_2 + E_1) + r_2^2(E_2 + 3E_1))r_1^2 P}{2E_1 r(r_2^2(E_2 + 3E_1) + r_1^2(3E_2 - E_1))}, & r_1 \le r \le r_2 \\ \dfrac{6r_1^2 r_2^2 P}{r(r_2^2(E_2 + 3E_1) + r_1^2(3E_2 - E_1))}, & r \ge r_2 \end{cases} \quad (1)$$

The tissues at the distance of r from the center of the carotid artery move to the position of the distance of r+d(r) from the center of the carotid artery in accordance with the change in the internal pressure. The amount of displacement d is positive, thus, indicating expansion, when the amount of change P of the internal pressure is positive. The amount of displacement d is negative, thus, indicating contraction, when the amount of change P of the internal pressure is negative.

When $r=r_1$ is assigned to Equation (1), the amount of displacement $d_1$ of the carotid artery wall inner surface can be expressed by the following Equation (2).

$$d_1 = \frac{3(r_1^2(-E_2 + E_1) + r_2^2(E_2 + 3E_1))r_1^2 p}{2E_1 r_1(r_2^2(E_2 + 3E_1) + r_1^2(3E_2 - E_1))} \quad (2)$$

From the physiological perspective, it is known that the elastic modulus $E_1$ of the carotid artery and the elastic modulus of the surrounding tissues $E_2$ are not significantly different (see Non-Patent Documents 3 and 4). It is also known that a thickness W ($W=r_2-r_1$) of the carotid artery wall is about 0.73 mm for people in their 20's and 30's, about 0.79 mm for people in their 40's, about 0.98 mm for people in their 50's, about 1.00 mm for people in their 60's, and about 1.04 mm for people in their 70's (see Non-Patent Document 5). It can be stated that the thickness W is sufficiently thinner than the diameter of the carotid artery (6 to 12 mm) or the thickness of the surrounding tissues. In consideration of the foregoing, Equation (1) can be approximated by the following Equation (3).

$$d(r; r_1, d_1) = d_1 \frac{r_1}{r} \quad r \ge r_1 \quad (3)$$

Figure 6:
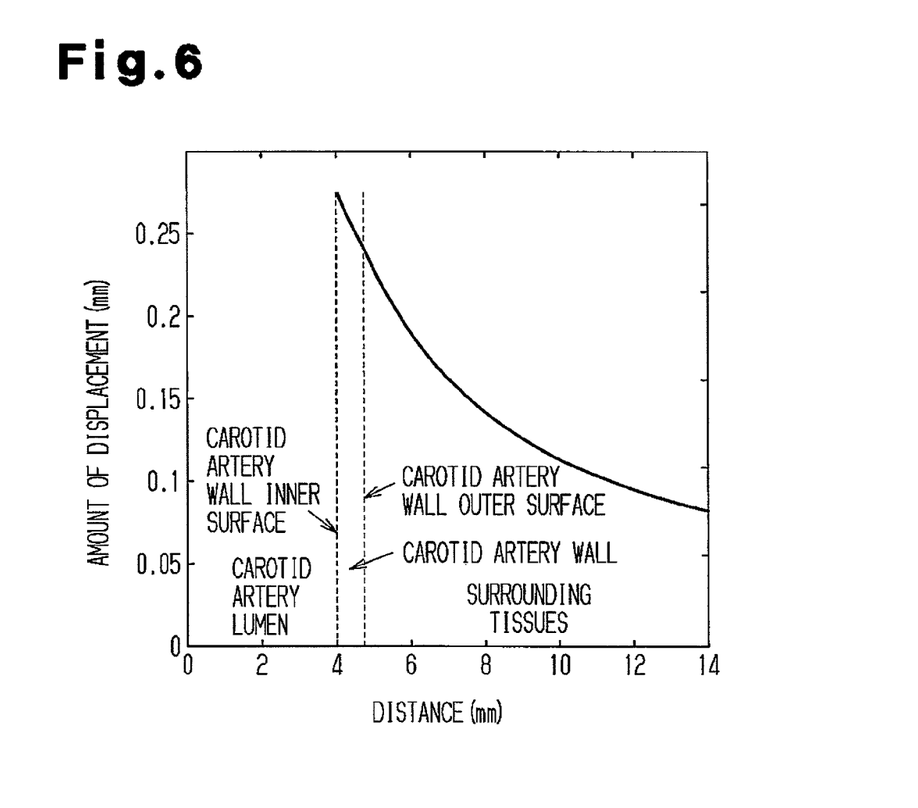
FIG. 6 is a graph showing the relationship between the distance r and the amount of displacement $d(r; P, r_1, r_2, E_1, E_2)$.
Figure 7:
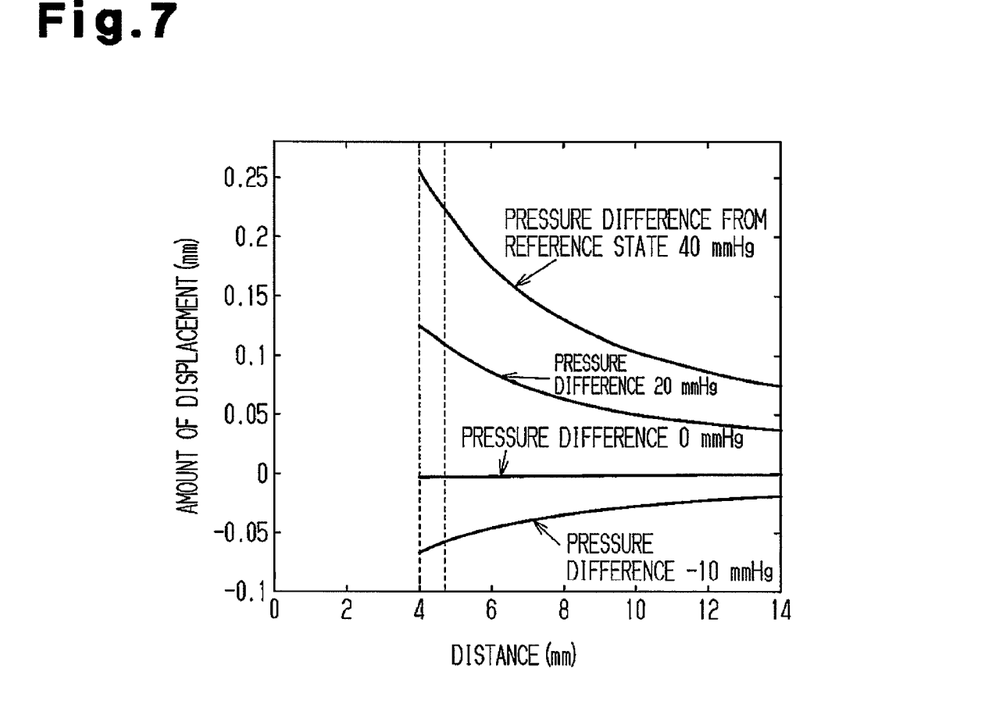
FIG. 7 is a graph showing the relationship between the distance r and the amount of displacement $d(r; P, r_1, r_2, E_1, E_2)$ when amounts of change P of blood pressure from a reference state are −10 mmHg, 0 mmHg, 20 mmHg, and 40 mmHg.

Equation (3) denotes that during heart contraction, or when the carotid artery and the surrounding tissues expand due to an increase in the blood pressure, the degree of expansion, or the amount of displacement, is inversely proportional to the distance r from the center of the carotid artery. FIG. 6 shows an example of the relationship between the distance r from the center of the carotid artery and the amount of displacement d(r; P, $r_1$, $r_2$, $E_1$, $E_2$) when $E_1$=200 kPa, $E_2$=100 kPa, $r_1$=4.0 mm, $r_2$=4.8 mm, and P=40 mmHg (5.3 kPa). FIG. 7 shows the relationship between the distance r and the amount of displacement d(r; P, $r_1$, $r_2$, $E_1$, $E_2$) when only the amount of change P of the internal pressure from the reference state is changed to −10 mmHg, 0 mmHg, 20 mmHg, and 40 mmHg. As shown in FIGS. 6 and 7, the relationship between the distance r and the amount of displacement d is expressed in inverse proportion regardless of the amount of change P of the internal pressure.
(Summary of Method for Tracking Heart Rate Variability of Carotid Artery Wall)

Since Equation (3) denotes that the amount of displacement d is inversely proportional to the distance r, if a point in the graphs shown in FIGS. 6 and 7, or the value of the distance r and the value of the amount of displacement d corresponding to the value of the distance r, such as the value of the inner radius $r_1$ of the carotid artery wall and the value of the amount of displacement $d_1$ of the carotid artery wall inner surface, is provided, the amount of displacement of the tissues at the distance of r from the center of the carotid artery including the surrounding tissues is completely determined.

When there is an ultrasound B-mode image Img1 (template image), from which the inner radius $r_1$ of the carotid artery wall can be obtained, if the image is transformed according to Equation (3), an ultrasound B-mode image Img2 (transformed template image) in another arbitrary blood pressure can be created in simulation. At that time, a parameter for controlling the degree of expansion or contraction is only $d_1$. If the value of the parameter $d_1$ used to create the transformed template image from the template image is determined to minimize the margin of error between the transformed template image and the image Img2 acquired by actual measurement, the determined value of $d_1$ is an estimated value of the amount of displacement $d_1$ of the carotid artery wall inner surface at a time from photographing of the image Img1 to photographing of the image Img2. More specifically, it can be estimated that the position of the carotid artery wall inner surface at the distance of $r_1$ from the center of the carotid artery in the image Img1 is displaced to the distance of $r_1+d_1$ from the center of the carotid artery in the image Img2. In other words, it can be estimated that the size of the inner radius of the carotid artery wall that has been $r_1$ in the image Img1 is changed to $r_1+d_1$ in the image Img2. If the same process is applied to all ultrasound B-mode images acquired by actual measurement, the time change in the inner diameter of the carotid artery wall can be tracked.

The point of the method is that the displacement of the surrounding tissues of the carotid artery caused by heartbeats is used to track the heart rate variability of the carotid artery wall. The area occupied by the surrounding tissues is much greater than the area occupied by the carotid artery wall in the ultrasound B-mode image. Therefore, the use of the displacement of the surrounding tissues caused by heartbeats can significantly improve the tracking accuracy of the heart rate variability of the carotid artery wall. Further improvement of the tracking accuracy is possible if the area occupied by the surrounding tissues in the ultrasound B-mode image is greater.

(Process of Image Processing Program)

Figure 9:
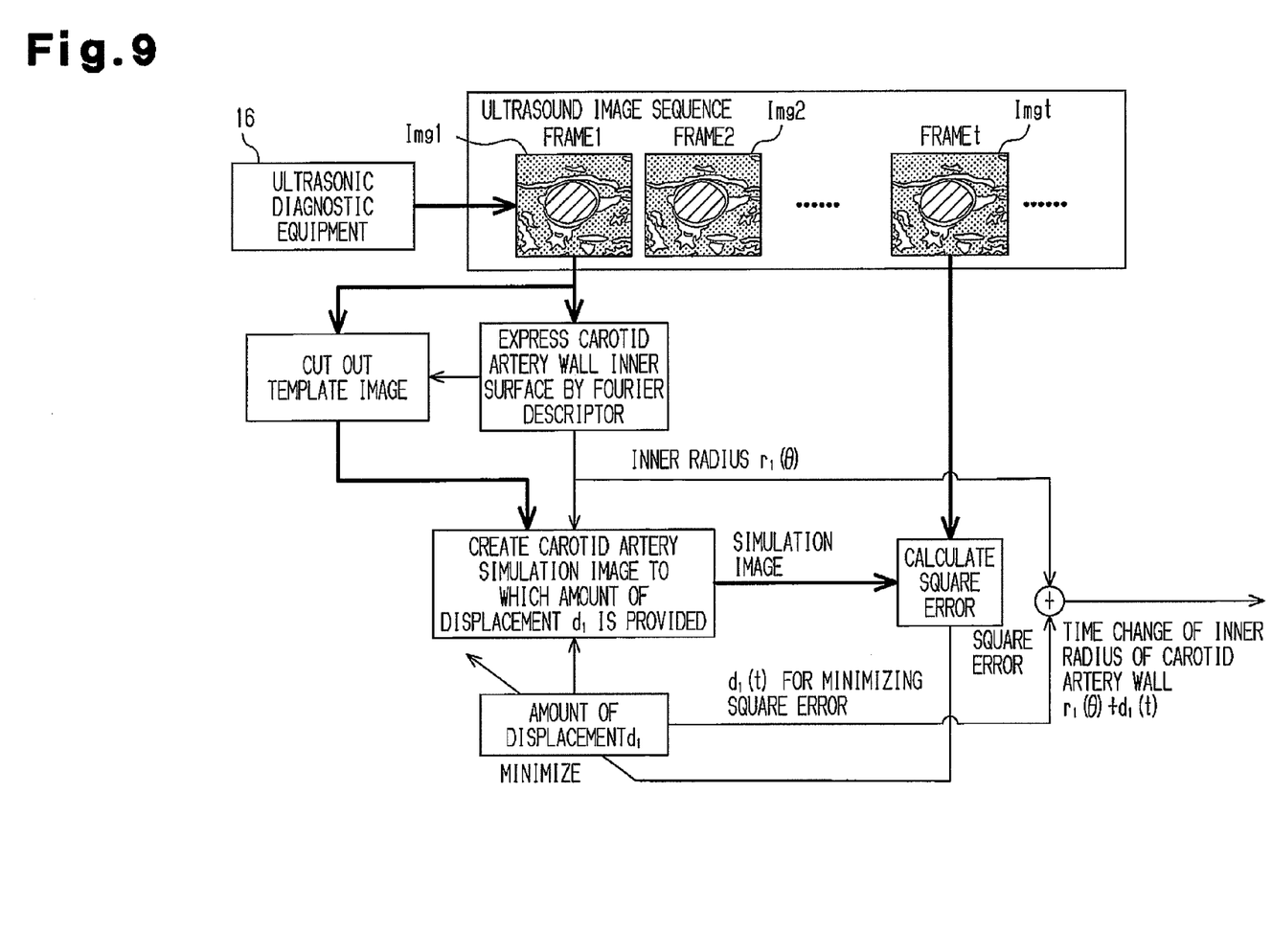
FIG. 9 is a conceptual diagram of a heart rate variability tracking method.

Next, a process of the image processing program executed by the CPU 41 of the image processing apparatus 11 will be described. The CPU 41 executes the process of steps S10 to S40 of FIG. 10 to perform heart rate variability tracking of the carotid artery. FIG. 9 shows a conceptual diagram of a heart rate variability tracking method.

Figure 10:
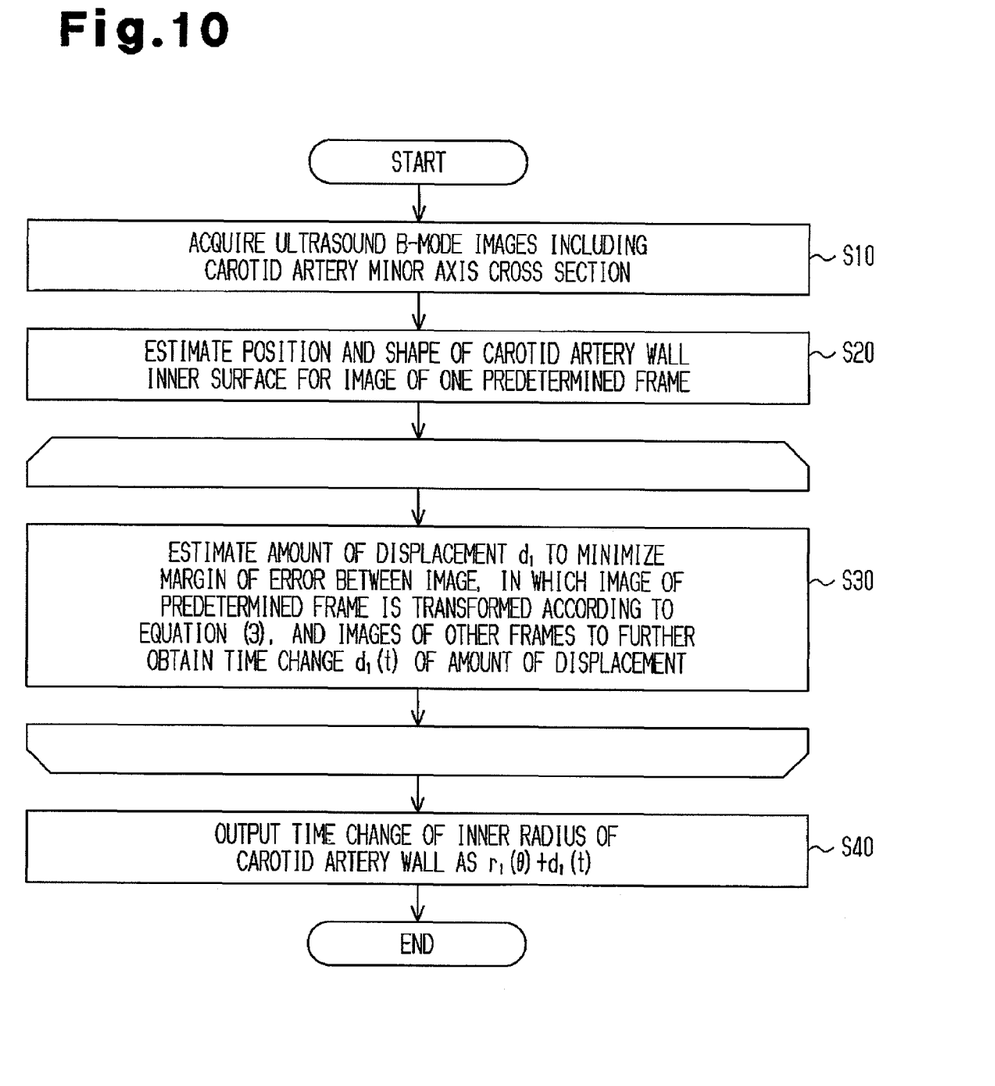
FIG. 10 is a flow chart of an image processing program executed by a computer of the image processing apparatus of FIG. 1.

In step S10, the CPU 41 measures and acquires ultrasound B-mode images of consecutive frames including carotid artery minor axis cross sections. The ultrasound B-mode images acquired by the CPU 41 are designated by I(x, y, t), x=1, . . . , Nx, y=1, . . . , Ny, and t=1, . . . Nt. Reference characters x, y, and t denote a pixel number in the horizontal direction, a pixel number in the perpendicular direction, and a frame number, respectively. To the pixel located at the upper left on each ultrasound B-mode image, x=1 and y=1 are provided. Reference characters Nx, Ny, and Nt denote the total number of pixels in the horizontal direction, the total number of pixels in the perpendicular direction, and the total number of frames, respectively. When one ultrasound B-mode image is focused, the image is expressed by I(x,y), x=1, . . . , Nx, and y=1, . . . , Ny.

In step S20, the CPU 41 selects an appropriate frame (predetermined frame) from the consecutive frames, and for the ultrasound B-mode image Img1 of the selected frame, estimates the position and the shape of the carotid artery wall inner surface, or more specifically, an inner radius $r_1(\theta)$ of the carotid artery wall (see FIG. 9). The inner radius $r_1(\theta)$ indicates a function related to the inner radius $r_1$ of the carotid artery wall including a direction $\theta$ ($0 \leq \theta \leq 2\Pi$) as a variable. The process of step S20 will be described in detail later.

In step S30, the CPU 41 transforms the ultrasound B-mode image of the predetermined frame according to Equation (3). In this case, the CPU 41 obtains an estimated value of the amount of displacement $d_1$ by minimizing the margin of error between the transformed image and the ultrasound B-mode images of the other frames. The time change $d_1(t)$ of the amount of displacement $d_1$ can be obtained by performing the same thing for the ultrasound B-mode images of all frames. The process in step S30 will be described in detail later.

In step S40, the time change of the inner radius of the carotid artery wall is set to $r_1(\theta)+d_1(t)$ and outputted to an output apparatus, such as the display 13 and the printer 14.

(Details of Process in Step S20)

In step S20 described above, the CPU 41 selects an appropriate frame from the consecutive frames and estimates the inner radius $r_1(\theta)$ of the carotid artery wall in the carotid artery minor axis cross section included in the ultrasound B-mode image Img1 of the selected frame. The frame to be selected is not particularly limited, and the frame can be randomly selected. Alternatively, a first frame, a frame clearly reflecting the carotid artery, a frame in which the carotid artery is in a contraction stage, or a frame in which the carotid artery is in an expansion stage may be selected.

The contour of the carotid artery wall inner surface is a complete circle or a little distorted circle. The contour of the carotid artery wall inner surface is modeled by a Fourier descriptor for expressing a closed curve. The Fourier descriptor is described in Non-Patent Document 2.

To express the contour of the carotid artery wall inner surface using the Fourier descriptor, coordinates x and y on the image are indicated by a complex number x+iy. Reference character i denotes a unit of imaginary number. Since the Fourier descriptor is used, a closed curve f(s) on a complex plane is expressed by the following Equation (4) using an intermediate variable s.

$$f(s) = \sum_{k=-K}^{K} c_k e^{i2\pi ks}, 0 \leq s \leq 1 \quad (4)$$

In Equation (4), $c_k$ denotes a Fourier descriptor as a parameter for determining the position and the shape of the closed curve, and K denotes an arbitrary integer. Although a more complicated closed curve can be expressed if the value of the integer K is greater, about K=5 can be set in the case of a contour of the carotid artery wall inner surface. However, the value of the integer K is not limited to this. Hereinafter, the Fourier descriptors defining the shape of the carotid artery wall inner surface will be collectively referred to as carotid artery parameters $p=\{c_k|k=0, \pm 1, \pm 2, \ldots, \pm K\}$.

Carotid artery lumens are areas surrounded by the closed curves f(s), and a set of pixels (x, y) located in the areas is designated by T. A set of pixels (x, y), in which the distance from the closed curve f(s) is equal to or smaller than a thickness W of the carotid artery wall, that is located outside the closed curve f(s) is designated by B. More specifically, the pixels (x, y) of the set B are located in an area corresponding to the carotid artery wall. The set B is provided by the following Equation (5).

$$B = \left\{ (x, y) \mid 0 < \min_{(x', y') \in T} \sqrt{(x' - x)^2 + (y' - y)^2} \leq W \right\} \quad (5)$$

In the image, the carotid artery wall is depicted in white because of a strong echo, and the carotid artery lumen is depicted in black because of a weak echo. More specifically, the pixel values are large in the pixels of the set B indicating the carotid artery wall, and the pixel values are small in the pixels of a set T indicating the carotid artery wall lumen. Therefore, for the carotid artery parameters p for determining the position and the shape of the carotid artery, an evaluation function E(p) expressed by the following Equation (6), which indicates the degree of probability of a carotid artery, is implemented.

$$E(p) = \frac{1}{|B|} \sum_{(x,y) \in B} I(x, y) - \alpha \frac{1}{|T|} \sum_{(x,y) \in T} I(x, y) - \beta g(A; A_{min}, A_{max}) \quad (6)$$

In Equation (6), both α and β are positive constants, and |•| denotes the number of elements of the set. In Equation (6), the greater, or the whiter, the pixel value at a position estimated to be a carotid artery wall, the greater the value of the first term of the right hand member is. The smaller, or the blacker, the pixel value at a position estimated to be a carotid artery lumen, the greater the value of the second term of the right hand member is. In the third term of the right hand member of Equation (6), g(A; Amin, Amax) is a function expressed by the following Equation (7).

$$g(A; A_{min}, A_{max}) = \begin{cases} (A - A_{min})^2, & A < A_{min} \\ 0, & A_{min} \leq A \leq A_{max} \\ (A - A_{max})^2, & A > A_{max} \end{cases} \quad (7)$$

In Equation (7), A denotes an area of the carotid artery lumen, thus, the number of pixels of the set T, and Amin and Amax denote a possible minimum value and a possible maximum value of the area of the carotid artery lumen, respectively. The third term of the right hand member of Equation (6) denotes a penalty when it is out of the possible range of the area of the carotid artery lumen. The values of Amin and Amax are preset based on samples of the images collected so far. For example, although Amin=20 (mm²) and Amax=110 (mm²) can be set, the values of Amin and Amax are not limited to these. As for the value of β in Equation (6), a sufficiently large positive number without causing a rounding error in the computer is selected. Although the value of α in Equation (6) depends on a ratio of strengths of echoes in the carotid artery wall and in the carotid artery lumen and specifications such as image output of the ultrasonic diagnostic equipment 16, it has already been made clear by preliminary tests that about α=2.0 can be selected.

Equation (6) can be rewritten by the following Equation (9) when a weight function w(x, y; p) is defined by the following Equation (8).

$$w(x, y; p) = \begin{cases} \frac{1}{|B|}, & (x, y) \in B \\ -\alpha \frac{1}{|T|}, & (x, y) \in T \\ 0, & \text{others} \end{cases} \quad (8)$$

$$E(p) = \sum_{x=1}^{N_x} \sum_{y=1}^{N_y} w(x, y; p) I(x, y) - \beta g(A; A_{min}, A_{max}) \quad (9)$$

Figure 8:
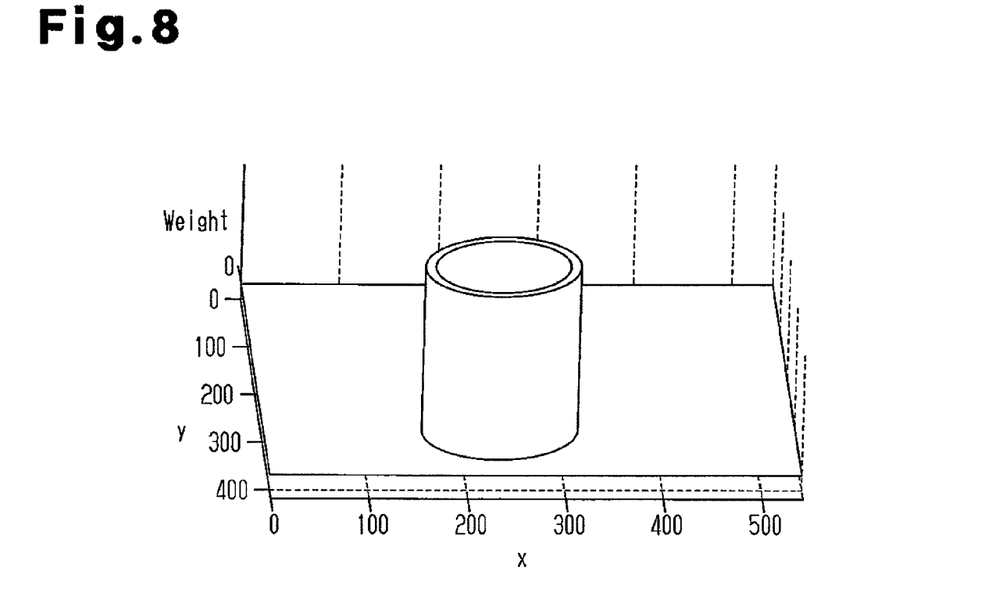
FIG. 8 is an explanatory diagram of a weight function w.

FIG. 8 shows an example of the weight function w(x, y; p). The value of the carotid artery parameter p for determining the position and the shape of the carotid artery in the ultrasound B-mode image I(x, y) can be determined to maximize the evaluation function E(p) provided by Equation (6) or (9). Such a value of parameter cannot be analytically obtained, but can be obtained using a non-linear optimization method such as a steepest descent method. Since there is no tissue that is circular in cross section similar to the carotid artery in the ultrasound B-mode image, it is unlikely to fall into the local solution.

The CPU 41 calculates the inner radius $r_1(\theta)$ of the carotid artery wall from the contour of the obtained carotid artery wall inner surface, thus, the closed curve f(s) (0≦s≦1), in the following manner. First, the center coordinates of the carotid artery is provided by (Re($c_0$), Im($c_0$)) using zero-dimensional Fourier descriptor $c_0$. Reference characters Re(•) and Im(•) denote a real part and an imaginary part of (•), respectively. The contour as seen from the center of the carotid artery is expressed by f(s)−$c_0$ (0≦s≦1). Therefore, the moving radius r(s) and the deflection angle θ(s) at the value of a certain intermediate variable s are expressed by the following Equations (10) and (11), respectively.

$$r(s) = |f(s) - c_0| = \sqrt{(\text{Im}(f(s) - c_0))^2 + (\text{Re}(f(s) - c_0))^2} \quad (10)$$

$$\theta(s) = \text{atan}\left(\frac{\text{Im}(f(s) - c_0)}{\text{Re}(f(s) - c_0)}\right) \quad (11)$$

Figure 11:
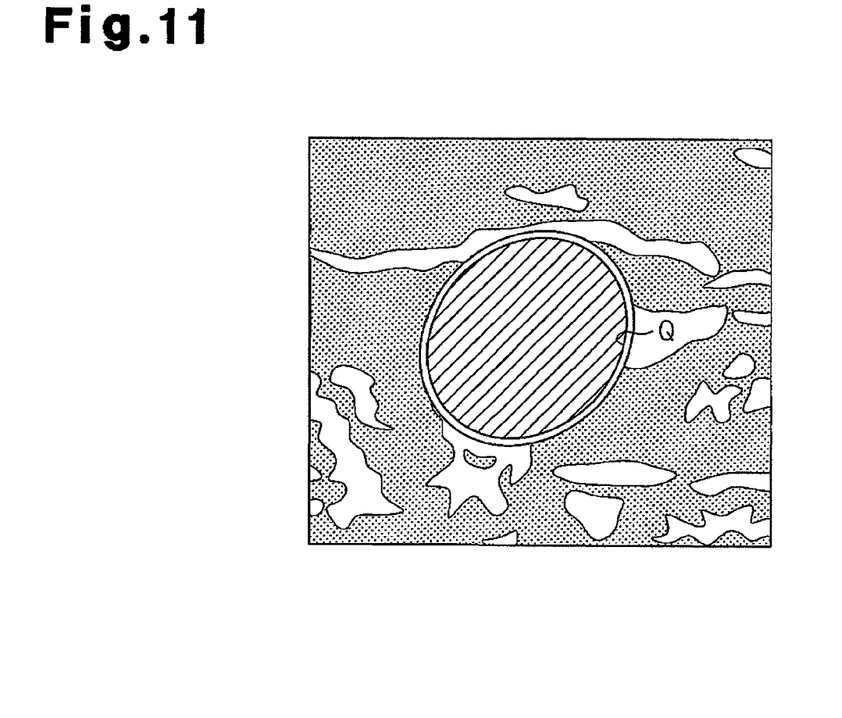
FIG. 11 is an explanatory diagram of a contour Q of a carotid artery wall inner surface estimated by a CPU of the computer.

If the intermediate variable s is removed, and r(s) is regarded as a function of θ(s), a polar coordinate display $r_1(\theta)$, 0≦θ≦2Π, of the shape of the carotid artery wall inner surface is obtained. FIG. 11 shows an example of a contour Q, or inner radius $r_1(\theta)$, of the carotid artery wall inner surface estimated by the CPU 41.

(Details of Step S30)

The CPU 41 cuts out an area properly including the estimated carotid artery wall inner surface and surrounding tissues from the ultrasound B-mode image Img1 of a predetermined frame. More specifically, a template image template (r, θ), in which the ultrasound B-mode image Img1 is represented in polar coordinates with the center of the carotid artery estimated in step S20 being an origin, is prepared.

The CPU 41 also prepares an image I(r, θ, t), in which an ultrasound B-mode image of an arbitrary frame (t-th frame) is represented in polar coordinates with the center of the carotid artery estimated in step S20 being an origin.

In principle, the image I(r, θ, t) of an arbitrary frame can be approximated by the following Equation (12) by transforming, or expanding or contracting, the template image by use of a proper value of $d_1$.

$$I(r, \theta, t) \cong \text{template}(r + d(r; r_1(\theta), d_1), \theta) \quad (12)$$

A square error J in the approximation based on Equation (12) is expressed by the following Equation (13). The CPU 41 determines the value of $d_1$ according to the following Equation (14) to minimize the square error J.

$$J = \sum_{r=0}^{R} \sum_{\theta=0}^{2\pi} (I(r, \theta, t) - \text{template } (r + d(r; r_1(\theta), d_1), \theta))^2 \quad (13)$$

$$d_1 = \underset{d1}{\arg\min} J \quad (14)$$

The determined value of $d_1$ indicates the amount of displacement of the carotid artery wall inner surface at time t (see FIG. 9).

Reference character r denotes a radius of an area used to evaluate the square error. If the value of r is increased, the area that can be used to estimate the heart rate variability of the carotid artery shape increases. As a result, the estimation accuracy is expected to rise. However, if the value of r is unduly increased, the nonuniformity of surrounding tissues and the like affects the estimation accuracy, and the estimation accuracy may be rather degraded. In this regard, it is preferable that the value of r be about two to three times the inner radius $r_1(\theta)$ of the carotid artery wall.

Figure 12:
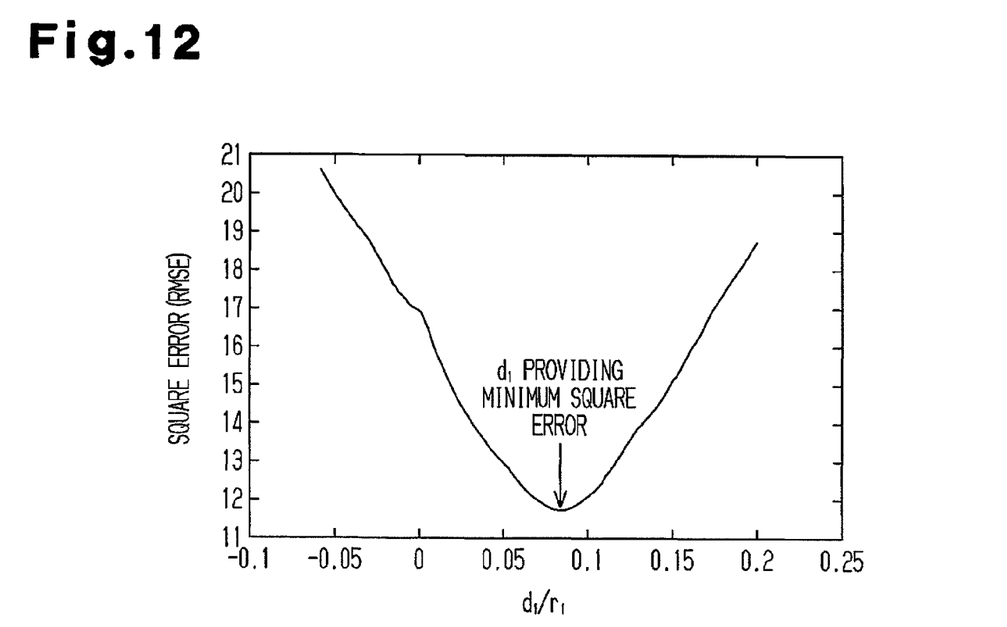
FIG. 12 is a graph showing the relationship between a change rate $d_1/r_1$ and a square error J.

FIG. 12 shows an example of the relationship between the change rate $d_1/r_1$ and the square error J in the ultrasound B-mode image of a certain frame. Reference character $r_1$ denotes an average of the inner radius of the carotid artery wall expressed by the following Equation (15).

$$r_1 = \frac{1}{2\pi} \int_0^{2\pi} r_1(\theta) d\theta \quad (15)$$

In the example shown in FIG. 12, the square error J is minimum at the change rate $d_1/r_1=0.08$. Therefore, $0.08 r_1$ is obtained as an estimated value of the amount of displacement $d_1$ of the carotid artery wall inner surface.

The CPU 41 applies similar processes to the acquired images of all frames excluding the image of the frame used as the template image to obtain the time change $d_1(t)$ of the amount of displacement. The time change of the inner radius of the carotid artery wall is provided as $r_1(\theta)+d_1(t)$.

(When Center of Carotid Artery is Fluctuated)

If the center of the carotid artery on the ultrasound B-mode image is deviated in each frame, the CPU 41 estimates not only $d_1$, but also a deviation $(x_0, y_0)$ of the center coordinates. In this case, an image $I'(r, \theta, t)$ is prepared, in which the center coordinates of the image $I(r, \theta, t)$ is shifted by $(x_0, y_0)$. Instead of Equations (13) and (14), the following Equations (16) and (17) are used.

$$J' = \sum_{r=0}^{R} \sum_{\theta=0}^{2\pi} (I'(r, \theta, t) - \text{template } (r + d(r; r_1(\theta), d_1), \theta))^2 \quad (16)$$

$$d_1 = \underset{d_1, x_0, y_0}{\arg\min} J' \quad (17)$$

When the template image template $(r, \theta)$ is expanded and contracted to create a template image template $(r+d(r; r_1(\theta), d_1), \theta)$, the position of a sample point (pixel) is also expanded and contracted. Therefore, the position of the sample point of the transformed template image is different from that of the original template image. Since the margin of error from the measured image $(r, \theta, t)$ cannot be evaluated in this state, re-sampling needs to be performed to match the sample points. Specifically, two-dimensional linear interpolation may be used, or various interpolation techniques, such as two-dimensional cubic interpolation and two-dimensional spline interpolation, used in morphing and the like may be used.

(Estimation Result)

A plurality of carotid artery ultrasound B-mode images are acquired from each of a 20-year-old healthy male and a 60-year-old healthy male. FIGS. 13(a) to 13(l) show results of estimation of the heart rate variability of the carotid arteries of both males by use of the acquired images, more specifically, results of estimation of the time change $r_1(\theta)+d_1(t)$ of the inner radius of the carotid artery ($\theta=0$ (degree), $0 \leq t \leq 4$ (second)). FIGS. 13(a) to 13(f) show the result of the 20-year-old healthy male, and FIGS. 13(g) to 13(l) show the result of the 60-year-old healthy male. In FIGS. 13(a) to 13(l), the vertical axis denotes the inner radius (mm) of the carotid artery, and the horizontal axis denotes the time (seconds). In FIGS. 13(a) to 13(f), the position where the heart rate variability of the carotid artery is being estimated is moved by 5 mm from a distal end (end near the brain) to a proximal end (end near the heart) in order of FIGS. 13(a) to 13(f). Similarly, in FIGS. 13(g) to 13(l), the position where the heart rate variability of the carotid artery is being estimated is moved by 5 mm from a distal end (end near the brain) to a proximal end (end near the heart) in order of FIGS. 13(g) to 13(l). The scale of the vertical axis of FIGS. 13(g) to 13(l) is different from the scale of the vertical axis of FIGS. 13(a) to 13(l).

Figure 13:
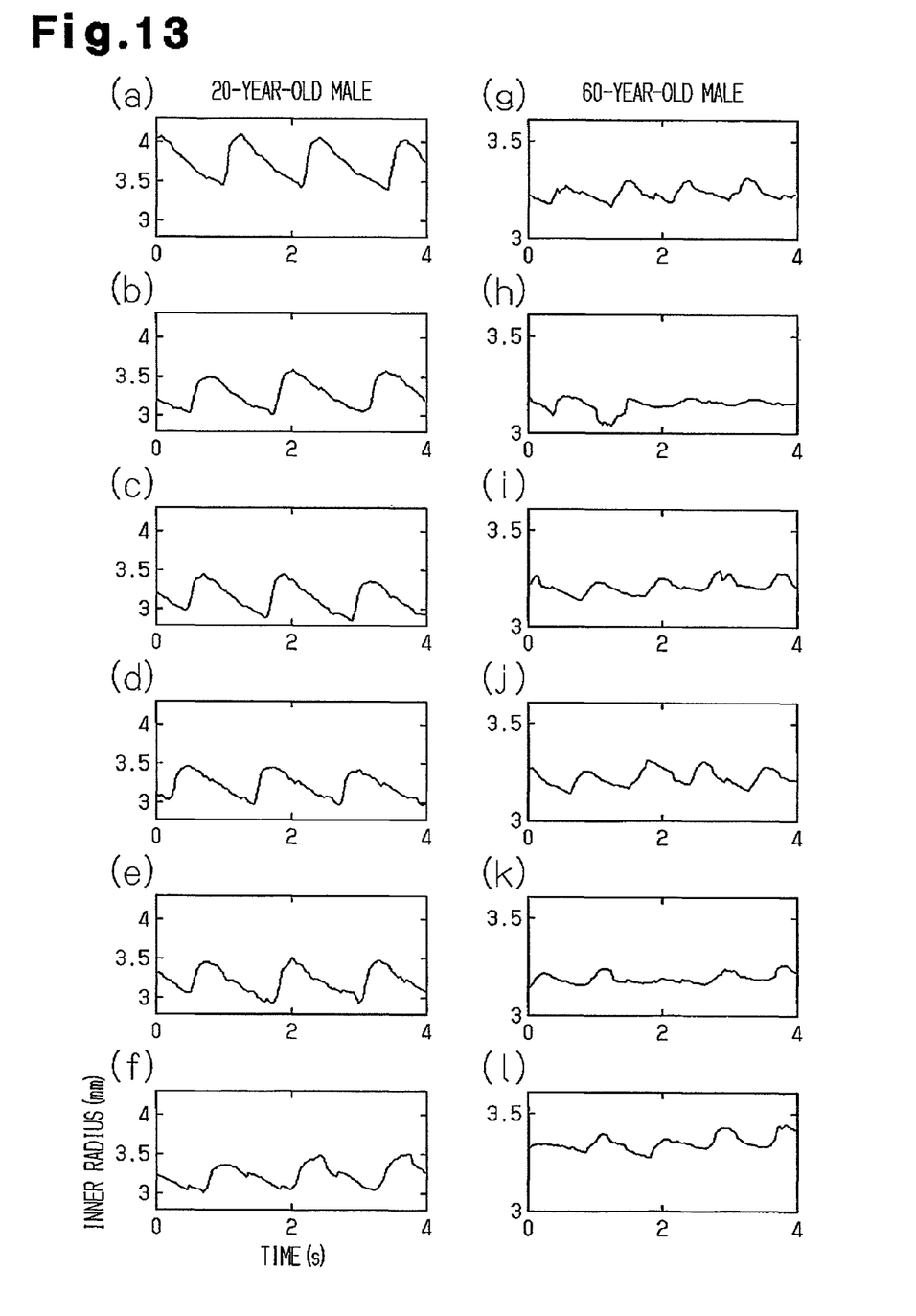
FIGS. 13(a) to 13(f) are graphs showing results of estimation of heart rate variability in a carotid artery of a 20-year-old healthy male.
FIGS. 13(g) to 13(l) are graphs showing results of estimation of heart rate variability in a carotid artery of a 60-year-old healthy man.

As can be seen clearly by comparing FIGS. 13(a) to 13(f) and FIGS. 13(g) to 13(l), the heart rate variability of the carotid artery of the 20-year-old male is large and clear, while the heart rate variability of the carotid artery of the 60-year-old male is small and lacks periodicity. In the case of the 20-year-old male, similar heart rate variability is shown in any cross section of the carotid artery. However, in the case of the 60-year-old male, the heart rate variability of the cross sections, for which the result is shown in FIGS. 13(h) and 13(k), is smaller than that of the other cross sections, and progression of local arteriosclerosis is predicted.

According to the present embodiment, the following advantages are obtained.

(1) Since the computer 12 functions as carotid artery wall estimation means, the image processing apparatus 11 of the present embodiment acquires ultrasound B-mode images of consecutive frames to estimate a carotid artery wall at a carotid artery minor axis cross section included in an ultrasound B-mode image of a predetermined frame. Since the computer 12 functions as heart rate variability tracking means, the image processing apparatus 11 uses, as a template image, the ultrasound B-mode image including the estimated carotid artery wall and surrounding tissues of the carotid artery wall and estimates the size of the diameter of the carotid artery wall so as to minimize a margin of error between a transformed template image, which is created by transforming the template image, and the acquired ultrasound B-mode image of each frame, thereby acquiring the time change of the carotid artery wall.

As a result, according to the present embodiment, even if there is local arteriosclerosis in a carotid artery, the heart rate variability of the carotid artery can be tracked with sufficient accuracy by using the ultrasound B-mode images. Particularly, although the size of one pixel of the ultrasound B-mode image is about 0.07 to 0.11 mm, which is not sufficiently high resolution, the heart rate variability of the carotid artery can be tracked with sufficient accuracy by taking not only the carotid artery, but also the surrounding tissues into consideration, and the meaning is significant. Furthermore, the ultrasound B-mode images can be acquired from general ultrasonic diagnostic equipment, and the versatility of the image processing apparatus 11 is high.

(2) The image processing apparatus 11 of the present embodiment determines the value of a carotid artery parameter for determining the position and the shape of a carotid artery so as to maximize an evaluation function indicating the degree of probability of a carotid artery, thereby estimating a carotid artery wall. In this case, the estimation of a carotid artery wall is easy.

(3) The image processing apparatus 11 of the present embodiment estimates a deviation if there is a deviation in the center of the carotid artery on the ultrasound B-mode image in each frame. In this case, even if there is a deviation in the center of the carotid artery on the ultrasound B-mode image in each frame, the estimation of a carotid artery wall is easy.

(4) The image processing program of the present embodiment causes the computer 12 to function to acquire ultrasound B-mode images of consecutive frames to estimate a carotid artery wall at a carotid artery minor axis cross section included in an ultrasound B-mode image of a predetermined frame. The image processing program also causes the computer 12 to function to use, as a template image, the ultrasound B-mode image including the estimated carotid artery wall and surrounding tissues of the carotid artery wall and to estimate the size of the diameter of the carotid artery wall so as to minimize a margin of error between a transformed template image, which is created by transforming the template image, and the acquired ultrasound B-mode image of each frame, thereby acquiring the time change of the carotid artery wall. As a result, the computer can function as an image processing apparatus capable of tracking the variability of the carotid artery associated with heartbeats with sufficient accuracy by using the ultrasound B-mode images, even if there is local arteriosclerosis in the carotid artery.

(5) The image processing program of the present embodiment causes the computer 12 to function to determine the value of a carotid artery parameter for determining the position and the shape of a carotid artery so as to maximize an evaluation function indicating the degree of probability of a carotid artery, thereby estimating a carotid artery wall. In this case, the estimation of the carotid artery wall is easy.

(6) The image processing program of the present embodiment causes the computer 12 to function to estimate a deviation if there is a deviation in the center of the carotid artery on the ultrasound B-mode image in each frame. In this case, even if there is a deviation in the center of the carotid artery on the ultrasound B-mode image in each frame, tracking of the heart rate variability of the carotid artery is easy.

(7) The ROM 42 of the present embodiment functions as a storage medium storing the image processing program. Since the CPU 41 of the computer 12 executes the image processing program, even if there is local arteriosclerosis in a carotid artery, the heart rate variability of the carotid artery can be tracked with sufficient accuracy by using the ultrasound B-mode images.

(8) Since the ultrasonic diagnostic equipment 16 of the present embodiment is connected to the image processing apparatus 11, advantages of (1) to (3) can be easily achieved.

The embodiment may be modified and configured as follows.

In place of the ROM 42, the storage device 44 may be used as the storage medium for storing the image processing program. Alternatively, the image processing program may be stored in a storage medium, such as a CD, a DVD, and a USB memory, and a driver device and the like may be used to load the stored image processing program from the storage medium to execute the program.

The result of analysis related to arteriosclerosis may be configured to be outputted only from one of the display 13 and the printer 14.

While the invention has been described in detail and with reference to specific embodiments thereof, it will be apparent to one skilled in the art that various changes and modifications can be made therein without departing from the spirit and scope thereof.

What is claimed is:

1. An image processing apparatus comprising:
a carotid artery wall estimation unit that acquires ultrasound B-mode images of consecutive frames to estimate a carotid artery wall at a carotid artery minor axis cross section included in an ultrasound B-mode image of a predetermined frame; and
a heart rate variability tracking unit that approximates, by the following Equation (1), a template image, which is prepared by representing the ultrasound B-mode image of the predetermined frame in polar coordinates and includes the estimated carotid artery wall and surrounding tissues of the carotid artery wall, to an image, which is prepared by representing each ultrasound B-mode image of the other frames in polar coordinates and determines the amount of displacement of the inner surface of the carotid artery wall according to the following Equation (2) or (3) so as to minimize a square error, which is expressed by the following Equation (4) or (5), thereby acquiring a time change of the carotid artery wall, $$I(r, \theta, t) \cong \text{template}(r + d(r; r_1(\theta), d_1), \theta) \qquad \text{Equation (1)}$$

$$d_1 = \underset{d1}{\text{argmin}} J \qquad \text{Equation (2)}$$

$$d_1 = \arg \underset{d_1, x_0, y_0}{\min} J' \qquad \text{Equation (3)}$$

$$J = \sum_{r=0}^{R} \sum_{\theta=0}^{2\pi} (I(r, \theta, t) - \text{template}(r + d(r; r_1(\theta), d_1), \theta))^2 \qquad \text{Equation (4)}$$

$$J' = \sum_{r=0}^{R} \sum_{\theta=0}^{2\pi} (I'(r, \theta, t) - \text{template}(r + d(r; r_1(\theta), d_1), \theta))^2, \qquad \text{Equation (5)}$$

wherein r denotes the distance from the center of the carotid artery, $\theta$ denotes the direction and is no less than 0 and no more than $2\pi$, t denotes a frame number, d(r) denotes the amount of displacement of the carotid artery and the surrounding tissues, $r_1$ denotes an inner radius of the carotid artery wall, $d_1$ denotes the amount of displacement of the carotid artery wall inner surface, and $x_0$ and $y_0$ denote a deviation of the center of the carotid artery.

2. The image processing apparatus according to claim 1, wherein the carotid artery wall estimation unit determines the value of a carotid artery parameter for determining the position and the shape of the carotid artery so as to maximize an evaluation function indicating the degree of probability of a carotid artery, thereby estimating the carotid artery wall.

3. The image processing apparatus according to claim 1, wherein if there is a deviation in the center of the carotid artery on the ultrasound B-mode image in each frame, the heart rate variability tracking unit also estimates the deviation.

4. Ultrasonic diagnostic equipment being connected to the image processing apparatus according to claim 1, generating an ultrasound B-mode image based on an echo signal obtained through transmission and reception of ultrasound by a probe, and outputting the generated ultrasound B-mode image to the image processing apparatus.

5. A non-transitory computer readable medium having stored thereon a computer executable image processing program which, when executed, causes a computer to implement:
- a carotid artery wall estimation unit that acquires ultrasound B-mode images of consecutive frames to estimate a carotid artery wall at a carotid artery minor axis cross section included in an ultrasound B-mode image of a predetermined frame; and
- a heart rate variability tracking unit that approximates, by the following Equation (1), a template image, which is prepared by representing the ultrasound B-mode image of the predetermined frame in polar coordinates and includes including the estimated carotid artery wall and surrounding tissues of the carotid artery wall, to an image, which is prepared by representing each ultrasound B-mode image of the other frames in polar coordinates and determines the amount of displacement of the inner surface of the carotid artery wall according to the following Equation (2) or (3) so as to minimize a square error, which is expressed by the following Equation (4) or (5), thereby acquiring a time change of the carotid artery wall, $$I(r, \theta, t) \cong \text{template}(r + d(r; r_1(\theta), d_1), \theta) \quad \text{Equation (1)}$$

$$d_1 = \arg\min_{d_1} J \quad \text{Equation (2)}$$

$$d_1 = \arg\min_{d_1, x_0, y_0} J' \quad \text{Equation (3)}$$

$$J = \sum_{r=0}^{R} \sum_{\theta=0}^{2\pi} (I(r, \theta, t) - \text{template}(r + d(r; r_1(\theta), d_1), \theta))^2 \quad \text{Equation (4)}$$

$$J' = \sum_{r=0}^{R} \sum_{\theta=0}^{2\pi} (I'(r, \theta, t) - \text{template}(r + d(r; r_1(\theta), d_1), \theta))^2, \quad \text{Equation (5)}$$

wherein r denotes the distance from the center of the carotid artery, $\theta$ denotes the direction and is no less than 0 and no more than $2\pi$, t denotes a frame number, d(r) denotes the amount of displacement of the carotid artery and the surrounding tissues, $r_1$ denotes an inner radius of the carotid artery wall, $d_1$ denotes the amount of displacement of the carotid artery wall inner surface, and $x_0$ and $y_0$ denote a deviation of the center of the carotid artery.

6. The non-transitory computer readable medium according to claim 5, wherein the carotid artery wall estimation unit determines the value of a carotid artery parameter for determining the position and the shape of the carotid artery so as to maximize an evaluation function indicating the degree of probability of a carotid artery, thereby estimating the carotid artery wall.

7. The non-transitory computer readable medium according to claim 5, wherein if there is a deviation in the center of the carotid artery on the ultrasound B-mode image in each frame, the heart rate variability tracking unit also estimates the deviation.

* * * * *